United States Patent [19]

Sekido et al.

[11] Patent Number: 4,832,818
[45] Date of Patent: May 23, 1989

[54] AIR/FUEL RATIO SENSOR

[75] Inventors: Satoshi Sekido; Takeshi Takeda, both of Kawasaki; Sohji Tsuchiya, Tsukui, all of Japan

[73] Assignee: Matsushita Electric Industrial Co., Ltd., Osaka, Japan

[21] Appl. No.: 135,300

[22] Filed: Dec. 21, 1987

[30] Foreign Application Priority Data

Dec. 19, 1986 [JP] Japan .................. 61-304166
Dec. 19, 1986 [JP] Japan .................. 61-304167

[51] Int. Cl.$^4$ ............................................. G01N 27/46
[52] U.S. Cl. .................................... 204/412; 204/421; 204/424; 204/426
[58] Field of Search ................ 204/1 S, 412, 421–429

[56] References Cited

U.S. PATENT DOCUMENTS

| Re. 28,792 | 4/1976 | Ruka et al. | 204/427 |
|---|---|---|---|
| 3,922,204 | 11/1975 | Tseung et al. | 204/421 |
| 4,345,985 | 8/1982 | Tohda et al. | 204/426 |
| 4,374,468 | 2/1983 | Takeshita et al. | 62/333 |
| 4,487,680 | 12/1984 | Logothetis et al. | 204/427 |
| 4,601,883 | 7/1986 | Sekido et al. | 422/94 |
| 4,692,429 | 4/1985 | Sekido et al. | 502/303 |

Primary Examiner—T. Tung
Attorney, Agent, or Firm—Wenderoth, Lind & Ponack

[57] ABSTRACT

An air/fuel ratio sensor to be used for controlling the ratio between the air and fuel through the detection of the air and the fuel in the exhaust gas of gas and oil combustion appliances, automobile engines or the like. The air/fuel ratio sensor has a first electrode on one face having porous zirconia electrolytic plate of through-holes, a second electrode containing at least electron $-O^{2-}$ ion mixed conductor on the other face. The controlling of the air/fuel ratio from the excessive fuel to the excessive air may be performed with a high S/N ratio under conditions ranging from excessive fuel to excessive air, through the measurement of the changes in the electric resistance of the second electrode by the third electrode provided on the second electrode. The sensor is simple in construction and is small and thin.

12 Claims, 3 Drawing Sheets

AIR/FUEL RATIO SENSOR

BACKGROUND OF THE INVENTION

The present invention relates to an air/fuel ratio sensor which is inserted into the exhaust gases of a gas appliance, an oil appliance or an automobile engine to detect the ration between the air and the fuel so as to control it.

Generally, a sensor of the concentration cell type which has a platinum black electrode on both sides of a stabilized or a partially stabilized zirconia electrolytic plate is known. Suppose the oxygen partial pressures on both the electrodes are respectively $P'O_2$ and $P''O_2$, the sensor causes such electromotive force E shown in the following equation (1) between both the electrodes.

$$E = RT/4F \cdot \ln(P'O_2/P''O_2) \quad (1)$$

wherein R is a gas constant, T is an absolute temperature, and F is a Faraday constant.

Accordingly, when the temperature T and the electromotive force E are measured with one electrode being exposed to the atmosphere, which is approximately constant in oxygen partial pressure as in air, the oxygen partial pressure on the other electrode may be detected.

In order to determine the oxygen partial pressure in the exhaust gas, a cylindrical pipe 101 blocked at one end is composed of zirconia electrolyte as shown in FIG. 1, electrodes 102, 103 made of platinum black connected with an anode terminal 104 and a cathode terminal 105 inside and outside it, and they are inserted into the exhaust pipe from the blockade side, so that the measuring operation is effected with the electrode 102 on the inner side being exposed to the air, the electrode 103 on the outer side being exposed to the exhaust gas. However, in the sensor of this concentration cell type, the electromotive force varies in proportion to the logarithm of the oxygen partial pressure, so that it is suitable when the oxygen partial pressure in the exhaust gas varies through units with the composition as the border as it is in the detection of the equivalent point of the combustion. However, as the electromotive force is small in change when the controlling operation is performed through the detection of an arbitrary air/fuel ratio, a high precision of the S/N ratio can not be realized.

In order to optionally detect the air/fuel ratio, the above portion of the external electrode 103 is covered with porous film 106 made of $Al_2O_3$ or $MgAl_2O_4$ as shown in FIG. 1, the DC voltage is applied from the terminals 104, 105 between both the electrodes 102, 103 to measure the diffusion limit current. As the diffusion limit current il changes in proportion to the oxygen partial pressure $P'O_2$ in the exhaust gas as shown in the following equation (2), the arbitrary air/fuel ratio may be detected through the measurement of it.

$$il = 4FDAP'O_2/l \quad (2)$$

wherein D is a diffusion constant of oxygen gas, A is the total of the sectional area of holes in the porous film 106 covering the external electrode 103, l is film thickness. Among these constants, D changes depending upon temperatures, so that the applied DC voltage by which the diffusion limit current is provided must be required to be increased more, depending upon the temperature, when the temperature is lower as shown in FIG. 2. To avoid such a complication in controlling DC application voltage, a heater 107 which is connected with the terminal 108 has to keep the temperature approximately constant.

Also, the construction shown in FIG. 3 is known as the other conventional diffusion limit current type sensor. In FIG. 3, an oxygen pump cell 111 made of zirconia electrolytic plate has electrodes 112, 113 provided on both faces thereof. A detection cell 114 made of the zirconia electrolytic plate has electrodes 115, 116 on both faces thereof. A heater 118 is buried in the base plate 117. A spacer 119, a spacer 120 are respectively interposed between the oxygen pump cell 111 and the detection cell 114, and between the detection cell 114 and the base plate 117. Diffusion gap 121 is provided between the oxygen pump cell 111 and the detection cell 114, and an air layer 122 is provided between the detection cell 114 and the base plate 117. A gas introduction hole 123 is formed in the oxygen pump cell 111.

In this sensor, the current of the oxygen pump cell 111 is previously settled to a fixed value and direction, and a fuel injection is controlled by a potential of the detection cell 114.

However, in the conventional construction shown in FIG. 1, the temperature of the exhaust gas considerably changes through the operating conditions as in an automobile. It is difficult to keep the sensor temperature constant at high speed. In the sensor, the controlling operation can not be performed in the case of fuel excess.

In the conventional construction shown in FIG. 3, the problems of the conventional embodiment shown in FIG. 1 may be removed. However, the construction may be made complex and larger as the detection cell 114 is provided separately from the pump cell 111. Also, using air electrode as a reference electrode of the detection cell 114 gives a difficult to provide for equipment.

SUMMARY OF THE INVENTION

Accordingly, an object of the present invention is to provide an air/fuel ratio sensor wherein the control of the air/fuel ratio from fuel excess to the air excess may be performed, in a condition high in S/N ratio, by the strict temperature control, the fast control may be controlled, and further, the construction may be made simpler, smaller and thinner.

In accomplishing this object, according to the preferred embodiment of the present invention, there are provided technical means of the present invention which include a porous stabilizing or partially stabilizing zirconia electrolytic plate made of through-holes, a first electrode which is provided on one face of this porous zirconia electrolytic plate and a second electrode which is provided on the other face of the porous zirconia electrolytic plate are composed of a mixed sinter member made of electron $-O^{2-}$ ion mixed conductor (which is $0 \leq X \leq 1, \delta \leq 0.5$) and $SrTiO_3$ which is a grain separating agent or a sinter member wherein at least one kind of element selected from Ag series, Pd series, or Pt series is added as an electric charge moving reaction catalyst to the electron $-O^{2-}$ ion mixed conductor and the grain separating agent, a third electrode for measuring the electric resistance provided on the second electrode, a gas impermeable base plate provided with the heater, a gas sealing material for preventing the entry of the gas, together with the base plate, which does not pass through the porous zirconia electrolytic plate to the second electrode.

In the present invention, the mixed conductor, which is porous through the zirconia electrolytic plate, is used for at least the second electrode between the first and second electrodes provided on both sides of this zirconia electrolytic plate, so that it may work as the catalyst of the equilibrium reaction between the reducing gas and the oxygen, and the resistance variation of the second electrode may detect that the atmosphere is the equivalent composition of the combustion. Accordingly, the construction is simplified, and the temperature of the sensor is not required to be set within the narrow range. Also, the controlling operation is effected so that the fuel supply may be throttled when the resistance of the second electrode has been detected to be in the high resistance region, and the air/fuel ratio which is high in the S/N ratio may be controlled.

Also, as the first electrode of the present invention, the porous platinum black, or a mixed sinter member made of

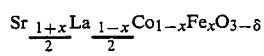

(which is electron $-O^{2-}$ ion mixed conductor (which is $0 \leq X \leq 1$, $\delta \leq 0.5$) and $SrTiO_3$ which is a grain separating agent or/and a sinter member wherein at least one kind of element selected from Ag series, Pd series, Pt series is added as an electric charge transfer reaction catalyst to the electron $-O^{2-}$ ion mixed conductor and the grain separating agent, as in the second embodiment, are preferable.

BRIEF DESCRIPTION OF THE DRAWINGS

These and other objects and features of the present invention will become apparent from the following description taken in conjunction with the preferred embodiment thereof with reference to the accompanying drawings, in which.

DETAILED DESCRIPTION OF THE INVENTION

Figure 1:
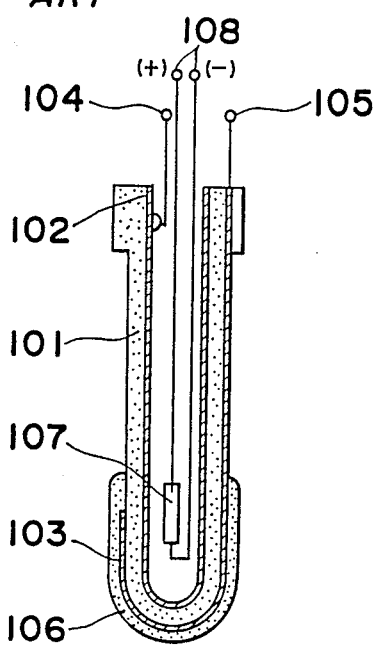
FIG. 1 is a sectional view of a conventional type of diffusion limit current sensor.
Figure 2:
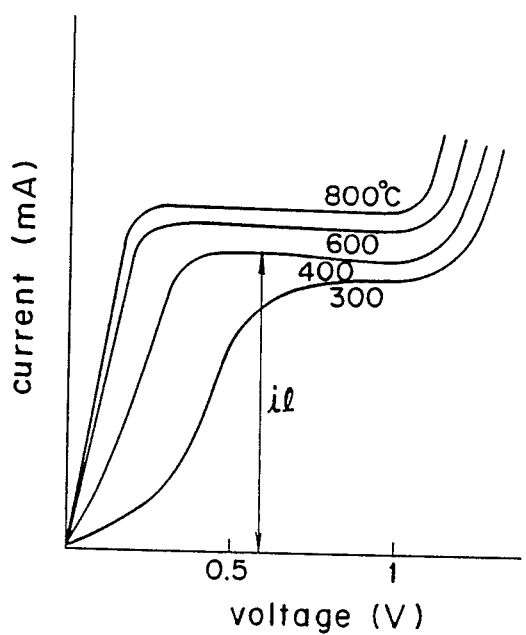
FIG. 2 is a view showing the current-voltage relationship at each temperature in the sensor of FIG. 1.
Figure 3:
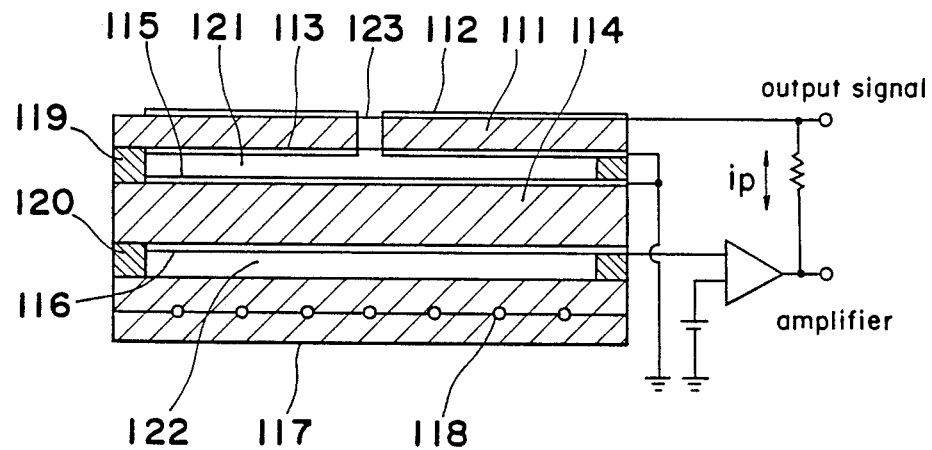
FIG. 3 is a sectional view showing a diffusion limit current sensor of improved type in another conventional embodiment.

Before the description of the present invention proceeds, it is to be noted that like parts are designated by like reference numerals throughout the accompanying drawings.

Figure 4:
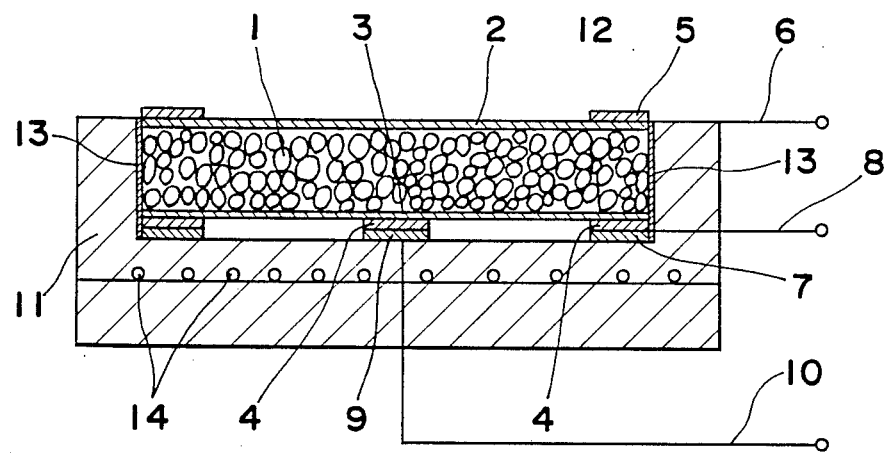
FIG. 4 is a sectional view showing an air/fuel ratio sensor in one embodiment of the present invention.

Referring now to the drawings, there is shown in FIG. 4 a sectional view of an air/fuel ratio sensor in one embodiment of the present invention. The air/fuel ratio sensor generally includes a disc-shaped porous stabilized or a partially stabilized zirconia electrolytic plate 1 (hereinafter referred to as zirconia electrolytic plate) which is perforated through, a first electrode 2 which is provided on one face of the zirconia electrolytic plate 1 to be exposed to the exhaust gas, a second electrode 3 provided on the other face of the zirconia electrolytic plate 1, the first and second electrode 2 and 3 are made of a mixed sinter member or a sinter member. The mixed sinter member is made of

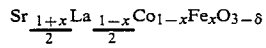

($0 \leq x \leq 1$, $\delta \leq 0.5$), which is an electron $-O^{2-}$ ion mixed conductor, and $SrTiO_3$ which is a grain separating agent. The sintered member comprises at least one element selected from the group consisting of, the Pd series, and the Pt series, added as an electric charge transfer reaction catalyst to the electron $-O^{2-}$ ion mixed conductor and a grain separating agent. As evident from the Periodic Table, Pd, Rh and Ru are in the Pd series while Pt, Ir and Os are in the Pt series. A third electrode 4 is provided in, for example, the center shape on the second electrode to measure the electrode resistance of the second electrode 3, this electrode is made of platinum. A terminal 5 is disposed on the first electrode 2 to flow the pump current between the first electrode 2 and the second electrode 3, the terminal 5 being connected with a led 6. A terminal 7 is provided on the second electrode 3 to flow the pump current to the second electrode 3 or to measure the resistance of the second electrode 3, with the terminal 7 being connected with a lead 8. A terminal 9 is provided on the third electrode 4 to measure the resistance of the second electrode 3, the terminal 9 being connected with a lead 10. A base plate 11 is made of a sapphire impermeable to gas, with zirconia electrolytic plate 1, the second electrode, third electrode, and terminal 7, 9 being accommodated in the concave portion 12. A gas sealing material 13 made of ceramic cement, etc. is interposed between the zirconia electrolytic plate 1 and base plate 11. It sealingly covers the second electrode 3 so that the gas, except for gas which passes through the zirconia electrolytic plate 1, may be prevented from penetrating into the second electrode 3. A heater 14, which is buried in the base plate 11, heats the entire sensor to a predetermined temperature (500° C. or higher when the charge transfer reaction catalyst is not added to the second electrode 3, 350° C. or higher when it is added).

The stabilized or partially stabilized zirconia electrolytic plate of the present embodiment is provided by the addition of Y, Ca, etc. to the zirconia.

The operation of the embodiment will be described hereinafter.

A current flows into a zirconia electrolytic plate 1 by the first 2 and second electrode 3, and the oxygen gas becomes ionized at the first electrode 2 on the side of the cathode, and is taken into the zirconia electrolytic plate to move to the second electrode 3 on the side of the anode, where it is discharged as oxygen again. In this case, the speed of moving from the cathode side (first electrode 2) onto the side of the anode (second electrode 3) is proportional to the value of current. This operation is referred to as an oxygen pump, as it operates like a pump, the fundamental principle of which is well known.

In the present invention, the zirconia electrolytic plate 1 is porous and perforated through, with mixed conductors being used as the first electrode 2 and the second electrode 3.

In the case of less air/fuel ratio than an equivalent point, the exhaust gas contains a large amount of moisture. The moisture of the exhaust gas is reduced by the first electrode 2 (cathode side) and is received as the $O^{2-}$ ion. It moves in the zirconia electrolytic plate to arrive at the second electrode 3 on the side of the anode. It is reacted to at electrode 2 reducing gas (HC, CO or the like) which diffuses form a through the holes of the zirconia electrolytic plate 1, and is removed, so that the large influence is not applied upon the increase and decrease of the $O^{2-}$ ion among the lattices within the second electrode 3. An excessive degree of the reducing gas in the exhaust gas lowers, by a throttling operation, the supply of the fuel when the resistance is high, thus resulting in less reduction gas, which diffuses into the holes of the zirconia electrolytic plate 1 so as to soon reach the equivalent point in air/fuel ratio. When the air/fuel ratio exceeds the equivalent point, the amount of the oxygen in the exhaust gas widely increases. The oxygen partial pressure in the atmosphere of the second electrode 3 composed of the mixed conductor rises several orders of magnitude or more to rapidly reduce the electric resistance of the second electrode 3. It is detected by third electrode 4 when the resistance has been reduced, so as to increase the supply of the fuel, and the driving operation may be effected at the air/fuel ratio of the excessive fuel according to the pump current $i_R$.

At the air/fuel ratio with excessive oxygen, the excessive $O_2$ or $NO_x$ diffuses in the porous zirconia electrolytic plate 1. When the oxygen, which is discharged onto the exhaust side through the current flow in the reverse direction, is more than the oxygen portion of the $O_2$ and the $NO_x$ to be diffused, the electric resistance of the second electrode 3 becomes larger. When the oxygen is less than the oxygen portion, the electric resistance becomes smaller, so that the supply of the fuel is controlled correspondingly.

Suppose that the partial pressure of the excessive fuel in the exhaust gas is $P_R$, the pump current $i_R$ is expressed by the following equation (3).

$$i_R = 4FD_{RA}P_R/l \tag{3}$$

When the driving operation is effected with excessive oxygen in the air/fuel mixture the current iO in the reverse direction and performs the controlling operation likewise, and the operation may be performed by the following equation (4).

$$i_O = 4FD_OAPO_2/l \tag{4}$$

Figure 5:
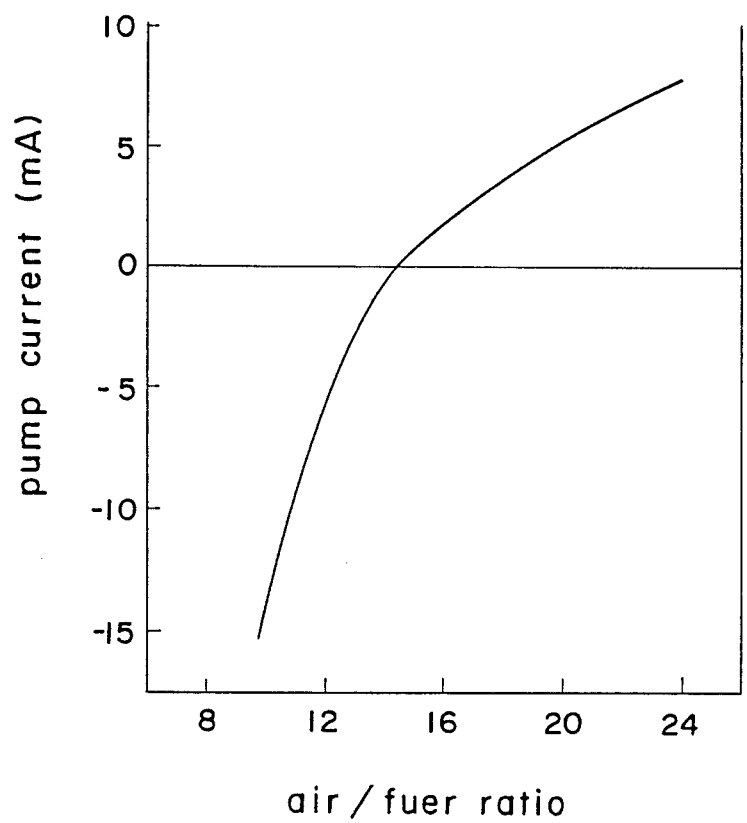
FIG. 5 is a chart showing the relationship between the air/fuel ratio of the sensor of the present invention and the pump current thereof.

The relationship between the air/fuel ratio to be controlled and the current flowing into the oxygen pump is shown in FIG. 5.

When the mixed conductor is used for both of the electrodes 2 and 3, it works as the catalyst of the equilibrium reaction between the reducing gas and the oxygen to increase the speed of the electrode reaction, so that the performance of the oxygen pump may be improved as compared with the prior use of Pt as an electrode as before. Also, the operation of the grain separating agent $SrTiO_3$ is useful to increase oxide ion conductivity $\delta O^{2-}$, and the addition of the catalytic element is useful in the speed increase of the electric charge transfer reaction so as to improve in the sensitivity and response property of the sensor.

The other embodiment of the present invention has the same construction as that of the embodiment shown in FIG. 1, with a porous platinum black being used as the first electrode 2 to be exposed as the exhaust gas.

Even in this case, as in the embodiment, the oxygen in the exhaust gas is reduced by the first electrode 2 into $O^{2-}$ ions. The electric resistance through the increase and decrease of the $O^{2-}$ ions among lattices is detected in the second electrode 3 which has moved in the zirconia electrolytic plate 1, so that the air/fuel ratio may be adjusted in accordance with the detection.

As porous platinum black is used for the first electrode in the embodiment, the oxygen activity increases. As the $O^{2-}$ ions are efficiently taken into the zirconia electrolytic plate 1, the sensitivity of the sensor may be increased.

The following properties are demanded as the second electrode 3 composed of the mixed conductor of the present embodiment.
(1) The operation as the catalyst of the equilibrium reaction between the reducing gas and the oxygen is provided.
(2) The balance between the external oxygen and the oxygen ions within the lattices is provided as quickly as possible in terms of sensitivity and response time.
(3) The thermal expansion coefficient is close to that of the zirconia electrolytic plate 1.

It is helpful to the above-described item (1) to use

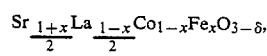

which is an electron $-O^{2-}$ ion mixed conductor. It is helpful to the increase of the above-described $\delta O^{2-}$ and the above-described item (3) to use the grain separating agent $SrTiO_3$. It is helpful to the electric charge transfer reaction speed of the above-described item (2) to add an electric charge transfer reaction catalyst element.

According to each of the above-described embodiments, the mixed conductor is used for at least the second electrode 3 of the porous oxygen pump. It is detected by the resistance changes thereof that the atmosphere is in the equivalent composition of the combustion. Thus, it becomes extremely simplified as compared with the conventional construction of each type, and it becomes simplified to make the size smaller and thinner. Also, the temperature of the sensor is not required to be set in a narrow range. Also, a current corresponding to the predetermined air/fuel ratio is flowed in the direction along which the controlling operation is effected between both the electrodes 2 and 3, namely, with the second electrode 3 provided on the cathode side in the case of excessive air, and with the second electrode 3 provided on the anode side in the case of excessive fuel. The fuel supply is throttled in control when the resistance of the second electrode 3 is high, so that the control of the air/fuel ratio, which is high in the S/N ratio, may be effected. Furthermore, as regards the sensitivity, the response property is superior, and the rapid control may be effected.

Examples will be described hereinafter.

EXAMPLE 1

As a zirconia electrolytic plate 1, methylcellulose is added at 20% to stabilized $ZrO_2$ powder ($-100$ mé) with moles of $Y_2O_3$ added thereto. It is molded into a shape 5 mm in diameter, 0.5 mm in thickness under the pressure of 2 t/cm$^2$, and is burned at 1400° C. for two hours. This percentage of voids is approximately 45%. After the sintering operation, the first and second electrodes are prepared by hydrogen flame spraying of a mixture of Sr0.65La0.35 Co0.7Fe0.3O3−δ and SrTiO3, the molar fraction of 0.4:0.6, on both side of the zirconia electrolytic plate 1. A plurality of units are manufactured. Half of them are heated at approximately 150° C. They are heated at 900° C. for thirty minutes and the saturated acetone solution of PdCl2·H2O is sprayed and are thermally decomposed. Pt paste is provided by screen printing as the third electrode 4 and terminal of the second electrode 4' on the second electrode 3 of the units. They are burned at 900° C. for thirty minutes. Leads 6, 8 and 10 made of Pd are connected by the pastes of the Pt, which becomes the terminals 5, 7 and 9 with respective electrodes 2 and 4. It is accommodated into the concave portion 12 of the base plate 11 made of sapphire having a heater 14. The second electrode 3 is completely sealed with hard glass, which is gas sealing material 13.

TRIAL MANUFACTURE EXAMPLE 2

As a zirconia electrolytic plate 1, methylcellulose is added at 20% to stabilized ZrO2 powder (−100 mé) with moles of Y2O3 added thereto. It is molded into 5 mm in diameter, 0.5 mm in thickness under pressure of 2 t/cm², and is burned at 1400° C. for two hours. The percentage of voids is approximately 45%. After the sintering operation, the second electrode 3 is prepared by hydrogen flame spraying of a mixture, the molar fraction of 0.4:0.6 on one face of the zirconia electrolytic plate 1. A plurality of units are manufactured. Half of them are heated at approximately 150° C. and the saturated acetone solution of PdCl2·H2O is sprayed. They are heated at 900° C. for thirty minutes and are thermally decomposed. Pt paste is provided by screen printing as the third electrode 4 and terminal of the second electrode 4' on the second electrode 3 of the units. They are burned at 900° C. for thirty minutes. The Pt paste is provided by the screen print as the first electrode 2 on the other face of the zirconia electrolytic plate 1 and is burned for thirty minutes at 900° C. Leads 6, 8 and 10 made of Pd are connected by the pastes of the Pt, which becomes the terminals 5, 7 and 9 with respective electrodes 2 and 4. It is accommodated into the concave portion 12 of the base plate 11 made of sapphire having a heater 14. The second electrode 3 is completely sealed with hard glass, which is a gas sealing material 13, and serves as the sensor.

These sensors are inserted into the exhaust manifold of an automobile. The operation is effected with the air/fuel ratio changed, with the current flowing into the heater 13 for the heating operation. The pump current is scanned with the electrode 3 as the anode when the resistance of the second sealed electrode 3 is high, and with the electrode as the cathode when the resistance is low and the value of the pump current which rapidly changed in the resistance of the electrode 3 is obtained. The current value is constant independently on temperature with 500° C. or more when the Pd is not added or with 350° C. or more when it is added. It is found out that the current value is determined, as in FIG. 5, only with air/fuel ratio. It is found from the fact that if the fuel supply is to be throttled when the resistance of the second electrode is high, with the current corresponding to the air/fuel ratio to be controlled in advance being flowed through the oxygen pump, the controlling operation may be effected into the predetermined air/fuel ratio.

As is clear from the foregoing description, according to the arrangement of the present invention, first and second electrodes are provided on both faces of the porous stabilizing or partially stabilizing zirconia electrolytic plate of through-holes. At least the second electrode is composed, on the other face, of the mixed sintered member made of

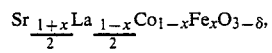

which is an electron −O²− ion mixed conductor, and SrTiO3 which is a grain separating agent or the sintered member, which comprises at least one element selected from the group consisting of the Ag, Pd series and the Pt series added as the electric charge transfer reaction catalyst to the electron −O²− ion mixed conductor and the grain separating agent. A third electrode for measuring the electric resistance is provided on the second electrode. A gas impermeable base plate provided with a heater, a gas sealing member, together with the base plate, for preventing the penetration of the gas, which does not pass through the porous zirconia electrolytic plate to the second electrode, are provided to detect the resistance changes of the second electrode. The second electrode has a function of promoting an equilibrium reaction between the reducing gas and the oxygen gas, and is capable of providing equilibrium as much as possible, between the external oxygen and the oxygen ion within the lattice with respect to the sensitivity, response property, with the thermal expansion coefficient being close to that of the porous zirconia electrolytic plate. Therefore, the construction is simplified, may be made thinner and smaller with the sensor temperature not being required to be set within a narrow range. Also, the supply of the fuel may be controlled so as to be throttled when the resistance of the second electrode has been detected to be in the high resistance region, so that the air/fuel ratio, which is high in the S/N ratio, may be controlled and, further, the fast control may be performed.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:
1. An air/fuel ratio sensor comprising:
   a porous stabilized or partially stabilized zirconia electrolytic plate having through-holes,
   first and second electrodes respectively provided on each side of said porous zirconia electrolytic plate and said electrodes comprising a sintered mixture of an electron −O²− ion mixed conductor and a grain separting agent SrTiO3,
   a third electrode provided on said second electrode for measuring the electric resistance of said second electrode responsive to said air/fuel ratio,
   a gas impermeable base plate provided with a heater, said base plate having a concave portion having therein said first electrode, said zirconia plate, said second and said third electrodes,
   a gas sealing material for preventing the entry of the gas from the combustion of said air and said fuel into said second electrode, except through said first electrode, means for flowing combustion products of a mixture of said air and said fuel between said first and second electrodes, and means for flowing electric current between said first and second electrodes, said sensor being capable of detecting the variation of values of resistance of said second electrode relative to said first electrode.

2. The air/fuel ratio sensor in accordance with claim 1 wherein the gas impermeable base plate is made of sapphire.

3. The air/fuel ratio sensor in accordance with claim 1 wherein said third electrode is made of platinum.

4. An air/fuel ratio sensor comprising:

a porous stabilized or partially stabilized zirconia electrolytic plate having through-holes, first and second electrodes respectively provided on both sides of the porous zirconia electrolytic plate and made of a sintered member comprising at least one element selected from the group consisting of Ag, the Pd series and the Pt series as an electric charge transfer reaction catalyst, an electron $-O^{2-}$ ion mixed conductor and a grain separating agent $SrTiO_3$, a third electrode which is provided on said second electrode for measuring the electric resistance of said second electrode responsive to said air/fuel ratio, a gas impermeable base plate provided with a heater, said base plate having a concave portion having therein said first electrode, said zirconia plate, said second and said third electrodes, a gas sealing material for preventing the entry of the gas from the combustion of said air and said fuel into said second electrode, except through said first electrode, means for flowing combustion products of a mixture of said air and said fuel between said first and second electrodes, and means for flowing electric current between said first and second electrodes, said sensor being capable of detecting the variation of values of resistance of said second electrode relative to said first electrode.

5. The air/fuel ratio sensor in accordance with claim 4 wherein the gas impermeable base plate is made of sapphire.

6. The air/fuel ratio sensor in accordance with claim 4 wherein the third electrode is made of platinum.

7. An air/fuel ratio sensor comprising:

a porous stabilized or partially stabilized zirconia electrolytic plate having through-holes, a first electrode provided on one face of the porous zirconia electrode plate and made of porous platinum black, a second electrode composed of a mixed sintered member which is provided on the other face of the porous zirconia electrolytic plate and made of

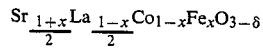

which is an electron $-O^{2-}$ ion mixed conductor ($0 \leq X \leq 1$, $\delta \leq 0.5$) and a grain separating agent $SrTiO_3$, a third electrode provided on said second electrode for measuring the electric resistance of said second electrode responsive to said air/fuel ratio, a gas impermeable base plate provided with a heater, said base plate having a concave portion having therein said first electrode, said zirconia plate, said second and said third electrodes, a gas sealing material for preventing the entry of the gas from the combustion of said air and said fuel into said second electrode, except through said first electrode, means for flowing combustion products of a mixture of said air and said fuel between said first and second electrodes, and means for flowing electric current between said first and second electrodes, said sensor being capable of detecting the variation of values of resistance of said second electrode relative to said first electrode.

8. The air-fuel ratio sensor in accordance with claim 4 wherein the gas impermeable base plate is made of sapphire.

9. The air/fuel ratio sensor in accordance with claim 4 wherein the third electrode is made of platinum.

10. An air/fuel ratio sensor comprising:

a porous stabilized or partially stabilized zirconia electrolytic plate having through-holes, a first electrode provided on one face of the porous zirconia electrolytic plate and made of a porous platinum black, a second electrode which is provided on the other side of said zirconia electrolytic plate and made of a sintered member comprising at least one element selected from the group consisting of Ag, the Pd series and the Pt series as an electric charge transfer reaction catalyst,

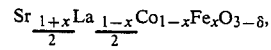

which is an electron $-O^{2-}$ ion mixed conductor ($0 \leq X \leq 1$, $\delta \leq 0.5$) and a grain separating agent $SrTiO_3$, a third electrode provided on said second electrode for measuring electric resistance of said second electric electrode responsive to said air/fuel ratio, a gas impermeable base plate provided with a heater, said base plate having a concave portion having therein said first electrode, said zirconia plate, said second and said third electrodes, a gas sealing material for preventing the entry of the gas from the combustion of said air and said fuel into said second electrode, except through said first electrode, means for flowing combustion products of a mixture of said air and said fuel between said first and second electrodes, and means for flowing electric current between said first and second electrodes, said sensor being capable of detecting the variation of values of resistance of said second electrode relative to said first electrode.

11. The air/fuel ratio sensor in accordance with claim 10 wherein the gas impermeable base plate is made of sapphire.

12. The air/fuel ratio sensor in accordance with claim 10 wherein a third electrode is made of platinum.

* * * * *